United States Patent [19]

Selhub et al.

[11] 4,167,556

[45] Sep. 11, 1979

[54] DETERMINATION OF TRANSCOBALAMINS

[75] Inventors: Jacob Selhub, Chicago, Ill.; Bracha Rachmilewitz; Nathan Grossowicz, both of Jerusalem, Israel

[73] Assignee: Yissum Research Development Company of the Hebrew University of Jerusalem, Jerusalem, Israel

[21] Appl. No.: 802,379

[22] Filed: Jun. 2, 1977

[51] Int. Cl.² .................... G01N 33/16; B65D 69/00
[52] U.S. Cl. ......................................... 424/1; 206/569
[58] Field of Search ........................ 424/1, 1.5, 12; 23/230 B; 206/569

[56] References Cited

PUBLICATIONS

Selhub et al., Febs Letters, vol. 44, No. 1, Aug., 1974, pp. 71–74.
Burger et al., J. of Biol. Chem., vol. 250, No. 19, Oct. 10, 1975, pp. 7700–7706.
Selhub et al., Proc. Soc. Ex. Bio. Med., 152, No. 2, 1976, pp. 204–209.
Selhub et al., Chemical Abstracts, vol. 81, No. 23, Dec. 9, 1974, pp. 205–206, Abstract No. 148007a.
Bruno et al., New Techniques in Tumor Location and Radio Immunoassay, Ed. Croll et al., John Wiley and Sons, New York, 1974, pp. 9–15.
Jacob et al., Journal of Laboratory and Clinical Medicine, vol. 83, No. 3, Mar., 1975, pp. 505–512.
Kumar et al., Proc. Soc. Ex. Bio. Med., 147, 1974, pp. 377–381.
Morelli et al., J. Lab. Clin. Med., vol. 89, No. 3, Mar., 1977.

*Primary Examiner*—Benjamin R. Padgett
*Assistant Examiner*—Christine M. Nucker
*Attorney, Agent, or Firm*—Andrew L. Klawitter

[57] ABSTRACT

A process for the quantitative determination of the transcobalamins TC-I, TC-II, and TC-III in serum. The process comprises incubating the serum with radiolabeled vitamin B-12, passing the resulting mixture through adsorption means, such as a charged cellulose filter or equivalent mini-column, for TC-II at a pH of about 8.5, adsorbing the remaining TC-I and TC-II components on a DEAE-cellulose type adsorbent, selectively desorbing the TC-III component with monopotassium phosphate solution of about 0.05 M and pH of about 4.6, and determining the radioactivity of each of the three transcobalamin fractions to indicate the individual and total unsaturated vitamin B-12 binding capacity of the three transcobalamins in the serum sample tested.

13 Claims, No Drawings

DETERMINATION OF TRANSCOBALAMINS

BACKGROUND OF THE INVENTION

1. Field of the Invention

The human serum contains at least three known binders of Vitamin B-12, namely the three transcobalamins designated as TC-I, TC-II, and TC-III. TC-I and TC-III are derived from granulocytes and both are alpha-globulins with a similar molecular weight, of about 120,000. They have a different electrical charge and hence differ in their electrophoretic mobility. TC-II is a beta-globulin of molecular weight of about 38,000 and it is derived mainly from the liver. The physiological functions of the three transcobalamins are not fully understood, but it is known that endogenous Vitamin B-12 is bound mainly to TC-I (about 85%), and TC-II binds about 15% of endogenous B-12 while TC-III seems to bind Vitamin B-12 only in vitro. Since TC-II binds small quantities of endogenous B-12 while it takes up the main part of Vitamin B-12 added to the serum in vitro, most of the unsaturated B-12 binding sites are located on TC-II (unsaturated B-12 binding capacity, UBBC). Vitamin B-12 is bound in the serum to the transcobalamins in a 1:1 molar ratio.

It is well known that certain pathological conditions are associated with significant specific changes in the level of the three transcobalamins in serum and that the determination of the Vitamin B-12 binding capacity of each of the three transcobalamins is an important tool in medical diagnosis. Amongst others, the quantitative determination of the B-12 binding capacity of the three transcobalamins is of value in the effective screening of certain malignant diseases and also in the monitoring of the treatment of these diseases. Amongst others, the determination of three transcobalamins is of value in:

A. Diagnosis, evaluation of treatment and monitoring of the course of myeloproliferative diseases [CML (chronic myelocytic leukemia), APL (acute promyeolocytic leukemia), polycythemia vera.]

B. Differentiation of leukemoid reactions and conditions manifested by non-leukemic leukocytosis.

C. Recognition of rapid malignant cell proliferation in lymphoma, sarcoma, Hodgkins Disease, acute leukemia, etc.

D. Evaluation of therapy and monitoring the course of malignant diseases (remission and relapse) such as sarcomas, acute leukemias, Hodgkins Disease, lymphomas etc.

E. Diagnosis and recognition of hepato-cellular damage.

The quantitative determination of B-12 binding capacity of the three transcobalamins may also be of value in the recognition, differentiation and monitoring of various other disorders.

2. Description of the Prior Art

The three transcobalamins present in human serum are difficult to separate and their quantitative determination is both complicated and time-consuming. The main problem is the similarity of electrophoretic properties of TC-II and TC-III and their similar behaviour on DEAE-cellulose separation.

The present determinations require at least two steps, namely:

a. DEAE-cellulose chromatography to separate TC-I from TC-II and TC-III and a Sephadex G-200 column to further separate TC-II from TC-III;

b. Adsorption of TC-II on charcoal and subsequent separation of TC-I and TC-III by a DEAE-cellulose chromatography;

c. Selective removal of TC-II from serum by Quso G-32 (a microfine precipitated silica) and subsequent separation of TC-I from TC-III on DEAE-cellulose;

d. Separation of TC-II on a G-200 column and subsequent separation of TC-I from TC-III by a DEAE-cellulose column.

e. Selective removal of TC-II by precipitation with ammonium sulfate and further separation of TC-I and TC-III from each other by DEAE-cellulose chromatography.

The above mentioned two-step procedures are rather laborious and require from two to three days to complete. Thus these are actually tools of a research laboratory and indeed the known procedures have not gained widespread acceptance as routine laboratory method in clinical laboratories.

SUMMARY OF THE INVENTION

The present invention relates to a simple and rapid process for the fractionation of the three transcobalimins from each other and for their quantitative determination. It further relates to means for carrying out this fractionation and determination. The invention further comprises means in kit form for the above purposes.

The process of fractionation comprises passing the mixture of the three transcobalamins through a sequence of charged cellulose filter media, such as cellulose nitrate filters or equivalent mini-columns, so as to separate TC-II from the other two transcobalamins; adsorbing the two other transcobalamins TC-I and TC-III on another medium such as a DEAE-cellulose filter, or mini-column, and selectively desorbing TC-III from the latter by means of a monopotassium phosphate solution of about 0.05 M at a pH of about 4.6. The entire procedure whether using filters or mini-columns is carried out in a rapid and continuous sequence of steps which can be completed within about one hour and a plurality of samples can be tested simultaneously.

Before passing the reaction mixture through the filters or equivalent adsorption media, the reaction mixture is incubated with an excess of $^{57}$Co B-12 of high specific activity, in a sodium borate buffer of about 0.1 M and at a pH of about 8.5. The radioactivity of the individual three transcobalamin fractions is determined and this gives a quantitative measure of the Vitamin B-12 binding capacity of each of the three transcobalamins. The adsorptions and desorptions are both specific and quantitative and thus provide a test of high accuracy and entirely adequate for clinical purposes.

DESCRIPTION OF THE PREFERRED EMBODIMENTS

The invention is described in the following way of example only in an illustrative manner, and it is clear that various modifications and changes can be resorted to in the details of the means used for the separation procedure.

I. MATERIALS

1. Cellulose nitrate filter discs, 25 mm in diameter (Schleicher and Schull, Dassel, Germany).
2. DEAE-Cellulose (DE-81) filter discs, 25 mm in diameter (The Whatman Biochemicals Ltd., Maidstone, Kent, England).

3. Millipore type filter holder apparatus for 25 mm discs (The Tamar Co., Jerusalem, Israel).
4. $^{57}$Co B-12, high specific activity (135–200 uCi/ug, the Radiochemical Centre, Amersham, Bucks, England). Batches of 10 uCi were diluted with water to a final concentration of 10,000 ph B-12/ml and stored in the refrigerator until ready for use.
5. Borate buffer, 0.1 M Sodium Borate adjusted to pH 8.5 with 10 M NaOH, prepared in glass distilled water and filtered through cellulose-nitrate filter to remove particles that may interfere with the assay.
6. Phosphate solution, 0.05 M monopotassium phosphate (pH 4.6) prepared in glass distilled water, and filtered through cellulose-nitrate filter as described above. The concentration of the phosphate is quite critical. No satisfactory separation can be obtained at lower or at higher concentrations.

II PROCEDURE (A) Determination of UBBC. The filter discs were arranged in a stack with one cellulose-nitrate disc which was previously immersed in distilled water, on top of three DE-81 discs. The stack was placed in the millipore filter holder and washed with glass distilled water before use. Duplicate samples of the serum (0.01 ml each) were incubated for 30 min at 37° (with excess of $^{57}$Co B-12 (100 pg/0.01 ml) and 0.2 ml 0.1 M Sodium Borate buffer (pH 8.5). After incubation, the mixture was diluted to 10–12 ml with the borate buffer and passed by applying vacuum through the filter stack. The excess unbound $^{57}$Co B-12 was removed by washing the filter twice, with 10 ml of the same borate buffer. The unsaturated B-12 binding capacity (UBBC, expressed in pg of $^{57}$Co B-12 bound per ml of serum, was calculated from the radioactivity retained by the stack.

(B) Determination of TC-I, II and III binding capacity. The duplicate samples of serum treated as described for the determination of UBBC and passed through the filter stack by applying vacuum. The excess unbound $^{57}$Co B-12 was removed as described above. Under these conditions TC-II is selectively and quantitatively adsorbed onto the cellulose-nitrate filter, while both TC-I and TC-III are adsorbed onto the DE-81 filters. After the filter stack was washed to remove the excess of $^{57}$Co B-12, the cellulose-nitrate filter was removed and counted (the first count). This count represents the unsaturated binding capacity of TC-II. The DE-81 filter stack was washed with 5 ml borate buffer and counted (the second count). This count represents the unsaturated binding capacity of TC-I and TC-III remaining on the DE-81 filter discs. Transcobalamins I and III were separated by washing the DE-81 filter stack with 15 ml of 0.05 M monopotassium phosphate solution (pH 4.6). The stack was again counted (the third count). This count represents the unsaturated binding capacity of TC-I adsorbed on the stack after TC-III was removed by the monopotassium phosphate solution. The unsaturated binding capacity of TC-III is given by the difference between the second and third counts.

The results obtained by the above procedure were checked with a number of the established laboratory procedures known in the art and a good agreement was obtained. The entire procedure according to the present invention can be carried out in about one hour and many samples can be tested simultaneously. Thus this novel method provides an important novel clinical test which is of great diagnostic value and which permits one to obtain results in an easy, speedy and efficient manner.

It ought to be stressed that various attempts have been made to separate transcobalamins by DEAE cellulose-chromatography. Various authors have reported experiments at pH 5.8 with 0.1 M sodium phosphate; at pH 6.35 with 0.06 M phosphate buffer; at pH 6.2 with 0.075 M phosphate buffer; at pH 6.3 with gradient of phosphate buffer 0.06 M and 1 M NaCl; a gradient of 0.01 M phosphate buffer (pH 8.0) and 0.3 M (pH 4.5). None of the above separation procedures was useful for an acceptable quantitative separation of the two transcobalamins I and III. The results obtained with sodium phosphate buffers, with monosodium phosphate and with potassium phosphate buffers were inconsistent and did not give the required separations. The concentration of 0.05 M monopotassium phosphate is quite critical. It may vary from about 0.045 to about 0.55, but at lower or higher concentrations inferior separations of TC-III from TC-I are obtained. The high pH of the borate buffer is a requisite for the selective adsorption of the TC-II on the cellulose nitrate filter.

Instead of the DEAE-cellulose filters there may be used DEAE-Sephadex mini-column. The filter media used according to the above description can of course be used in column form.

The present invention also relates to test means in kit form, comprising the necessary selective separation means, such as filter-column or stack, chemicals for the required solutions and $^{57}$Co Vitamin B-12 solution.

Results obtained indicate that various pathological changes can be readily differentiated by means of the results obtained by the above method of determination of TC-I, TC-II, and TC-III.

Extensive experiments were carried out with patients having various types of disease. The procedure used was as set out above. The results of the determinations is given in the following. The following summary of the results is grouped as follows:

Group 1: Deals with normals.
Group 2: Deals with chronic myeloid leukemia (CML) and promyelocytic leukemia (APL).
Group 3: Deals with Polyceythemia vera (PV) and leukocytosis.
Group 4: Deals with acute leukemia, Hodgkins disease and lymphoma.
Group 5: Deals with hepatocellular damage.

(a) Group 1: Normals

Table - A

| No | Patient Identificaton | $B_{12}$ pg/ml | UBBC pg/ml | TCI pg/ml | TCII pg/ml | TCIII pg/ml |
|---|---|---|---|---|---|---|
| 1 | E.G | 700 | 1884 | 301 | 1260 | 283 |
| 2 | Y. | 570 | 1764 | 317 | 1112 | 335 |
| 3 | Y.A | 650 | 2230 | 356 | 1696 | 178 |
| 4 | A.Z | 870 | 1605 | 224 | 1012 | 369 |
| 5 | R.M | 950 | 2058 | 205 | 1462 | 391 |
| 6 | R.Z | 550 | 1925 | 212 | 1501 | 212 |
| 7 | S.B | 800 | 1720 | 190 | 1204 | 326 |
| 8 | A.A | 500 | 1360 | 136 | 984 | 240 |
| 9 | Z.Y | 900 | 1760 | 229 | 1355 | 176 |
| 10 | O.Y | 540 | 1560 | 203 | 843 | 514 |
| 11 | H.D | 700 | 1400 | 196 | 868 | 336 |
| 12 | P.M | 750 | 1500 | 120 | 1185 | 195 |
| 13 | A.H | 700 | 1484 | 268 | 905 | 311 |
| 14 | S.A | 660 | 1545 | 171 | 1019 | 355 |
| 15 | B.A | 700 | 1760 | 246 | 1144 | 370 |
| 16 | R.A.H | 700 | 1500 | 165 | 945 | 611 |

Table - A-continued

| | | | | | | |
|---|---|---|---|---|---|---|
| 17 | P.G | | 800 | 1588 | 159 | 1032 | 397 |

From Table A, one can define the ranges of Vitamin $B_{12}$, UBBC and transcobalamins in normal cases to be as follows:

| | | |
|---|---|---|
| $B_{12}$ | 500–950 | pg/ml |
| UBBC | 1300–2250 | pg/ml |
| TCI | 100–350 | pg/ml |
| TCII | 800–1700 | pg/ml |
| TCIII | 175–600 | pg/ml |

(b) Group 2: CML and APL

Table - B

| No | Patient Identification | $B_{12}$ pg/ml | UBBC pg/ml | TCI pg/ml | TCII pg/ml | TCIII pg/ml | Remarks |
|---|---|---|---|---|---|---|---|
| 1 | R.M | 1500 | 6098 | 3780 | 1255 | 1063 | |
| 2 | A.R | 3000 | 6823 | 4571 | 1500 | 752 | |
| 3 | S.A | 2300 | 6352 | 3898 | 1674 | 780 | |
| 4 | C.P | 4000 | 3623 | 2174 | 1196 | 253 | |
| 5 | Z.S | 1300 | 3085 | 740 | 1666 | 679 | in remission |
| 6 | A.Y | 800 | 2235 | 290 | 1230 | 715 | in remission |
| 7 | P.H | 1000 | 2117 | 509 | 1025 | 583 | in remission |
| 8 | A.I | 1600 | 3970 | 1192 | 1627 | 1151 | |
| 9 | Y.M | 1140 | 3394 | 1086 | 1459 | 849 | |
| 10 | C.Z | 4000 | 2945 | 1537 | 1030 | 878 | |
| 11 | Z.B | 1400 | 2747 | 1100 | 1330 | 317 | |
| 12 | B.A | 2750 | 6461 | 3941 | 1163 | 1358 | |
| 13 | D.T | 3000 | 6740 | 3628 | 1550 | 1562 | |
| 14 | R.A | 3200 | 3660 | 1756 | 1574 | 330 | |

In CML and APL cases there is elevation in UBBC, due to increase in TCI binding capacity, resulting in high serum $B_{12}$ levels.

The increase in TCIII binding capacity is an expression of the chronicity of the disease, because of the more mature cells present in the population which produce mainly TCIII. The TCI binding capacity decreases during chemotherapy and this serves as a reliable criterion in the evaluation of the effect of the therapy. Patients in remission, show normal to slightly elevated ranges of TCI (patients Nos. 5–7). Thus, the test for TCI contributes to monitoring the course of chronic myeloid leukemia (remission, relapse and acute crisis) and the response to chemotherapy.

(c) Group 3: PV and leukocytosis cases

Table C

Polycythemia vera (PV) and leukocytosis

| No | Patient Identification | $B_{12}$ pg/ml | UBBC pg/ml | TCI pg/ml | TCII pg/ml | TCIII pg/ml | Remarks |
|---|---|---|---|---|---|---|---|
| 1 | M.P | 400 | 1933 | 270 | 870 | 793 | |
| 2 | M.S | 1250 | 3147 | 440 | 1320 | 1387 | |
| 3 | V.H | 700 | 3352 | 370 | 696 | 2013 | |
| | | 500 | 2941 | 299 | 964 | 1678 | following chemotherapy |
| 4 | P.Y | 900 | 3352 | 335 | 1173 | 1844 | |
| 5 | G.M | 870 | 2529 | 227 | 1466 | 836 | |
| 6 | A.C | 400 | 2076 | 228 | 1079 | 769 | |
| 7 | Y.Y | 650 | 2176 | 148 | 961 | 997 | |
| 8 | S.M | 550 | 3384 | 376 | 1522 | 1486 | |
| 9 | B.A | 750 | 6461 | 356 | 1609 | 4496 | |
| 10 | M.P | 900 | 2424 | 387 | 1284 | 753 | |
| 11 | B.A | 750 | 2852 | 370 | 1369 | 1113 | |
| 12 | K.P | 400 | 2360 | 295 | 979 | 1086 | |
| | | 950 | 1529 | 229 | 902 | 339 | following chemotherapy |
| 13 | A.F | 700 | 2289 | 183 | 1533 | 572 | |
| 14 | C.I | 200 | 1970 | 177 | 1319 | 474 | |
| 15 | I.H | 370 | 2294 | 137 | 1468 | 689 | |
| 16 | A.A | 700 | 2117 | 296 | 1587 | 234 | |
| 17 | H.P | 800 | 2000 | 280 | 1040 | 680 | |
| 18 | C.M | 1000 | 2424 | 387 | 1405 | 632 | |
| 19 | C.Z | 810 | 1888 | 170 | 1379 | 339 | |
| 20 | A.I | 400 | 2613 | 236 | 1672 | 705 | |
| 21 | M.G | 900 | 1558 | 202 | 898 | 460 | |

In PV and leukocytosis there is elevation in UBBC due to increase in TCIII binding capacity. No changes were noticed in $B_{12}$, TCI or TCII.

In active PV (PV in relapse) associated with increased leukocyte concentration there is an increase in TCIII serum concentration (patients Nos. 2,3,4,8,9, 11 and 12). In the non-active PV state with normal leukocyte concentration, TCIII is normal to slightly elevated (patients Nos. 1, 13–21). The TCIII binding capacity decreases during chemotherapy (patients Nos. 3 and 12). Thus, the test for TCIII contributes to monitoring the course of active (relapse) PV stages, the response to chemotherapy treatments, and monitoring the non-active PV stages as well. More important, serum TCIII binding capacity determination helps in differentiation of leukemoid reactions and conditions manifested by nonleukemic leukocytosis.

(d) Group 4: Acute leukemia, Hodgkins disease and lymphoma cases

Table - D

Acute leukemia cases

| No | Patient Identification | $B_{12}$ pg/ml | UBBC pg/ml | TCI pg/ml | TCII pg/ml | TCIII pg/ml | Remarks |
|---|---|---|---|---|---|---|---|
| 1 | I.A | 1000 | 3647 | 291 | 2918 | 438 | |
| 2 | P.M | 730 | 3763 | 452 | 2747 | 564 | |
| 3 | P.N | 900 | 7568 | 203 | 6760 | 605 | |
| | | 900 | 4018 | 201 | 3335 | 482 | Following chemotherapy |

Table - D-continued

Acute leukemia cases

| No | Patient Identification | $B_{12}$ pg/ml | UBBC pg/ml | TCI pg/ml | TCII pg/ml | TCIII pg/ml | Remarks |
|---|---|---|---|---|---|---|---|
| 4 | K.H | 750 | 6000 | 400 | 5180 | 420 | |
|  |  | 750 | 3037 | 273 | 2581 | 183 | Following chemotherapy |
|  |  | 450 | 2545 | 127 | 2188 | 230 | Following chemotherapy |
| 5 | M.S | 270 | 2935 | 376 | 2431 | 410 | |
|  |  | 370 | 1900 | 171 | 1349 | 380 | Following chemotherapy |
| 6 | Z.H | 850 | 3364 | 471 | 2422 | 471 | |
|  |  | 700 | 2360 | 306 | 1652 | 402 | Following chemotherapy |
| 7 | M.B | 900 | 3030 | 121 | 2545 | 364 | |
|  |  | 300 | 2000 | 140 | 1540 | 320 | Following chemotherapy |
|  |  | 450 | 1900 | 285 | 1240 | 375 | Following chemotherapy |
|  |  | 500 | 1360 | 136 | 984 | 240 | Following chemotherapy |
| 8 | B.A | 475 | 2650 | 291 | 1829 | 530 | |
|  |  | 600 | 2063 | 228 | 1583 | 247 | Following chemotherapy |
| 9 | H.M | 1000 | 2300 | 254 | 1771 | 276 | |
|  |  | 500 | 1700 | 173 | 986 | 571 | Following chemotherapy |
| 10 | Z.I | 580 | 2739 | 109 | 2492 | 137 | |
|  |  | 670 | 1834 | 129 | 1467 | 238 | Following chemotherapy |
|  |  | 700 | 2000 | 258 | 1442 | 300 | Following chemotherapy |
|  |  | 900 | 1760 | 229 | 1355 | 176 | Following chemotherapy |
| 11 | H.H | 200 | 2360 | 277 | 1959 | 123 | |
|  |  | 870 | 1930 | 368 | 1258 | 674 | Following chemotherapy |
| 12 | N.A.A | 1200 | 2000 | 180 | 1460 | 360 | Protracted course |
| 13 | A.H.N | 650 | 2100 | 280 | 1400 | 420 | Protracted course |
| 14 | Z.I | 600 | 1760 | 119 | 1330 | 311 | Protracted course |
| 15 | G.M | 1070 | 1868 | 280 | 1309 | 280 | Protracted course |

(e) Group 5: Hodgkins disease and lymphoma cases

Table - E

| No | Patient Identification | $B_{12}$ pg/ml | UBBC pg/ml | TCI pg/ml | TCII pg/ml | TCIII pg/ml | Remarks |
|---|---|---|---|---|---|---|---|
| 1 | B.S | 950 | 5300 | 380 | 4500 | 420 | |
|  |  | 500 | 1475 | 163 | 1012 | 300 | Following chemotherapy |
| 2 | Z.A | 720 | 4411 | 486 | 3514 | 411 | |
| 3 | I.P | 700 | 2615 | 235 | 2119 | 261 | |
| 4 | A.A | 900 | 3600 | 180 | 3096 | 324 | |
| 5 | V.V | 500 | 4176 | 126 | 3499 | 551 | |
| 6 | V.A | 1000 | 5100 | 204 | 4384 | 512 | |
| 7 | L.H | 850 | 4650 | 372 | 3787 | 491 | |
| 8 | A.A | 450 | 3500 | 175 | 2905 | 420 | |
| 9 | K.I | 700 | 4900 | 434 | 3800 | 666 | |
| 10 | S.V | — | 4500 | 180 | 4005 | 315 | |
| 11 | I.S | — | 2910 | 175 | 2270 | 465 | |
| 12 | S.B | — | 1500 | 150 | 1020 | 330 | Protracted course |
| 13 | S.Z | — | 2100 | 147 | 1680 | 273 | Protracted course |

Tables D and E relating to acute leukemias, Hodgkins disease and lymphomas in which there is increase in UBBC due to elevation in TCII binding capacity. No changes were noticed in $B_{12}$, TCI or TCIII. The increase in TCII is in direct proportion to the acuteness of the disease. Increase in serum TCII binding capacity without a change in Vitamin $B_{12}$ level may indicate an acute proliferation of malignant cells of any kind (such as acute leukemia, Hodgkins disease, lymphomas, etc). This finding may be useful in the recognition of rapid cell proliferation in malignant lymphoma and acute nondifferentiated leukemias. The TCII binding capacity decreases during chemotherapy and thus serves as a reliable criterion in the evaluation of the effect of the therapy. Patients during the protracted or remission course show normal ranges of TCII. However, during the proliferation of the malignant cells (the relapse stage) increase in TCII binding capacity is noticed. Thus, the test for TCII contributes to the monitoring of the relapse course of acute leukemias, Hodgkins disease, lymphomas, etc., the response to chemotherapy treatments and monitoring the protracted course or remission as well.

(f) Group 5: Hepatocellular damage

It is well established that increase in serum Vitamin $B_{12}$ bound mainly to TCII is characteristic to hepatocellular damage. The $B_{12}$ released from the damaged liver cells saturates TCII and part of the TCI. As a result, serum binding capacity (UBBC) is very low while endogenous $B_{12}$ bound to TCII is increased. Since the filter-stack technique determines the UBBC of the binders, in hepatic diseases the TCII will be very low. This phenomena is already well recognized and accepted as a valuable diagnostic aid.

SUMMARY

Determination of serum transcobalamins binding capacity is useful in diagnosis of the following diseases:

| Disease | Vitamin $B_{12}$ | UBBC of whole serum | Binding Capacity | | |
|---|---|---|---|---|---|
| | | | TCI | TCII | TCIII |
| CML and APL | elevation | elevation | elevation | normal | elevation[1] |
| PV and leukocytosis | normal | elevation | normal | normal | elevation |
| AML, Hodgkins disease lymphoma | normal | elevation | normal | elevation | normal |
| Hepatocellular damage | elevation | decrease | normal | decrease | normal |

[1] in chronic cases

Serum transcobalamins binding capacity determination is also useful in monitoring the relapse courses of these diseases, the response to chemotherapy treatments and monitoring the protracted or remission courses as well.

In summary, the three transcobalamins undergo specific quantitative changes during certain clinical pathological conditions. The research done on this subject during the last few years has proved beyond any doubt the clinical significance of the changes in the transcobalamins binding capacity. The determination of the various serum transcobalamins binding capacity is today an important tool in diagnosis as well as in evaluation of the effects of treatment.

What is claimed is:

1. A process for the quantitative determination of each of the three transcobalamins TC-I, TC-II, and TC-III in serum, which comprises incubating a predetermined quantity of serum with a solution of $^{57}Co$ Vitamin B-12, passing the resulting solution through adsorption means adapted to selectively adsorb TC-II on a charged cellulose filter or equivalent mini-column at a pH of about 8.5; adsorbing the TC-I and TC-III constituents on a cellulose filter of the DEAE-cellulose type or an equivalent mini-column; selectively desorbing the TC-III by means of a monopotassium phosphate solution of about 0.05 M and at a pH of about 4.6, and determining the radioactivity of each of the three transcobalamin fractions thus obtained, indicating the individual and total unsaturated B-12 binding capacity (UBBC) of the three transcobalamins.

2. A process according to claim 1, wherein the incubation is effected with 0.1 M sodium borate buffer of pH of about 8.5.

3. A process according to claim 1, wherein the solution of serum and $^{57}Co$ Vitamin B-12 is applied to the filters or equivalent mini-columns by application of reduced pressure.

4. A process according to claim 1, wherein $^{57}Co$ Vitamin B-12 not bound to transcobalamins is removed from the filters or equivalent mini-columns by means of borate buffer.

5. A process according to claim 1, wherein the TC-II is adsorbed on a cellulose nitrate filter or mini-column.

6. A process according to claim 5, wherein the TC-I and TC-III are adsorbed on a DEAE-cellulose filter or mini-column.

7. A process according to claim 1 wherein the TC-I and TC-III are adsorbed on a DEAE-cellulose filter or mini-column.

8. A kit for the quantitative determination of TC-I, TC-II, and TC-III, comprising, in combination, a container of $^{57}Co$ Vitamin B-12 solution, adsorption means for the separation of TC-II from combined TC-I and TC-III, and a container of monopotassium phosphate solution of about 0.05 M and pH of about 4.6.

9. A kit according to claim 8, wherein the adsorption means comprises a combination of a cellulose nitrate filter to quantitatively adsorb TC-II and DEAE-cellulose to quantitatively adsorb both TC-I and TC-III.

10. A kit according to claim 8, which additionally comprises a container of borate solution.

11. A kit according to claim 10, wherein the borate solution is about 0.1 M and at pH 8.5.

12. A kit according to claim 8, wherein the $^{57}Co$ Vitamin B-12 is of an activity of from 135–200 $\mu Ci/\mu g$.

13. A kit according to claim 9, wherein said DEAE-cellulose is in the form of a filter.

* * * * *